United States Patent
Katagihara et al.

(12)

(10) Patent No.: US 6,333,047 B1
(45) Date of Patent: *Dec. 25, 2001

(54) MOLDED CAPSULE SUPERIOR IN STRENGTH AND STABILITY AND METHOD FOR PREPARING SAME

(75) Inventors: Hiroshi Katagihara, Fuji; Yohichi Kinekawa, Shiga; Yoshinori Ueda, Yamanashi; Yukiko Yonemoto, Kyoto; Satoshi Sogawa, Fuji; Naofumi Kitabatake, Uji, all of (JP)

(73) Assignees: Daiichi Kasei Co., Ltd., Kyoto; Aliment Industry Co., Ltd., Yamanashi, both of (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/193,101

(22) Filed: Nov. 16, 1998

Related U.S. Application Data

(63) Continuation-in-part of application No. 08/947,039, filed on Oct. 8, 1997, now abandoned.

(30) Foreign Application Priority Data

May 9, 1997 (JP) .................................... 9-135853

(51) Int. Cl.[7] ................ A61K 9/48; A61K 9/64
(52) U.S. Cl. .............. 424/456; 424/451; 264/4.1; 426/140; 426/657
(58) Field of Search .................. 424/451, 456, 424/460; 264/4.1; 426/140, 657

(56) References Cited

U.S. PATENT DOCUMENTS

| 5,416,196 |   | 5/1995  | Kitabatake et al. . |
|-----------|---|---------|---------------------|
| 5,601,760 | * | 2/1997  | Rosenberg .         |
| 5,672,301 | * | 9/1997  | Orly et al. .       |
| 5,691,060 | * | 11/1997 | Levy .              |
| 5,756,136 | * | 5/1998  | Black et al. .      |

FOREIGN PATENT DOCUMENTS

| 0375852 A1  | 7/1990  | (EP) . |
| 0559425 A1  | 9/1993  | (EP) . |
| 0750854 A2  | 1/1997  | (EP) . |
| 02-22221 A  | 1/1990  | (JP) . |
| 06-189698 A | 7/1994  | (JP) . |
| 07-196478 A | 8/1995  | (JP) . |
| 96/40083    | 12/1996 | (WO) . |

OTHER PUBLICATIONS

European Search Report dated Aug. 11, 1998.

* cited by examiner

Primary Examiner—Thurman K. Page
Assistant Examiner—Brian K. Seidleck
(74) Attorney, Agent, or Firm—Morgan & Finnegan, L.L.P.

(57) ABSTRACT

A molded capsule having a capsule membrane which contains a Process Whey Protein together with at least one selected from the group consisting of scleroproteins, derived proteins and mucopolysaccharides. The capsule membrane may contain a plasticizer. The molded capsule has high membrane strength, exhibits stability even at high temperatures and high humidity, and is highly digestible. The molded capsule is prepared by using a die rolls encapsulating machine.

8 Claims, No Drawings

MOLDED CAPSULE SUPERIOR IN STRENGTH AND STABILITY AND METHOD FOR PREPARING SAME

This is a continuation-in-part of application Ser. No. 08/947,039 filed Oct. 8, 1997, now abandoned.

BACKGROUND OF THE INVENTION

The present invention relates to a molded capsule which can be stably obtained with a thin membrane, which is superior in collapsing property but causes substantially no caking nor deformation by the change of pressure, temperature, humidity or the like and which can be useful in foods, drugs and cosmetics and is high in safety.

Molded capsules have been conventionally used in various fields such as foods, drugs and cosmetics. However, the capsule membrane has been prepared mainly by mixing a hydrated and swollen gelatin with a plasticizer and then drying the mixture. Such a capsule can be prepared relatively easily and is high in transparency and excellent in beauty. However, it has many disadvantages as follows. (1) It requires a long period for the preparation and drying of the membrane material in its production. (2) It requires strict temperature control to avoid leakage of packed suspension, formation of so-called avec sphere by mutual adhesion of capsules and deformation. (3) In the storage of capsules, a low humidity causes lowering of strength of the membrane to easily damage it by impact. (4) A high humidity, a high temperature or shortage of releasing agent causes deformation and caking. (5) If the thickness of the membrane is made thin, the strength becomes insufficient. (6) The collapse in digestive organs is slow.

On the other hand, as a method for eliminating these disadvantages of capsule membrane, JP 02-22221 A discloses a method for the preparation of a capsule improved in sliding and collapsing property by using a natural calcium material.

However, this method reduces transparency of the capsule and cannot produce a product of excellent beauty and cannot fully accomplish reduction of manufacturing period, improvement in strength and prevention of avec sphere and deformation, disadvantageously.

An object of the present invention is to eliminate disadvantages of conventional capsules as described above and to provide a molded capsule, i.e., a soft gel capsule, which can be easily and stably prepared and prevents liquid leakage and occurrence of avec sphere and deformation and is rich in membrane strength and has a high stability against changes in pressure, temperature and humidity. Further, an object of the present invention is to make the capsule membrane thin and to make the size of the capsule small and as the result to give a capsule product which can be easily dosed and is high in collapsing property and softness and can be used widely in various fields such as foods, drugs and cosmetics and is superior in safety.

SUMMARY OF THE INVENTION

We solve the above problems by forming a capsule membrane containing "Process Whey Protein" which is obtained by heating milk whey protein under a specific condition.

Thus, the molded capsule of the present invention has a capsule membrane which contains "Process Whey Protein" together with at least one selected from the group consisting of scleroproteins, derived proteins and mucopolysaccharides. The capsule membrane may further contain a plasticizer.

DETAILED DESCRIPTION OF THE INVENTION

"Process Whey Protein" used in the present invention is prepared by a procedure in which low molecular weight compounds other than milk whey protein are substantially removed from milk whey which are a waste material from the manufacture of cheese, butter and casein by using milk as the raw material and then the pH of the product is adjusted to not higher than 4 or not lower than 6 and then heat-treated. For example, by using cheese whey formed in the manufacture of cheese, the low molecular weight compounds in milk whey are removed substantially by a dialysis or a chromatography and the product is heat-treated at a pH not higher than 4 or not lower than 6 to give the Process Whey Protein. For example, the method for the preparation of "Process Whey Protein" is disclosed in U.S. Pat. No. 5,416, 196 A and EP 0473270 B which are corresponding to JP 04-228036 A, JP 04-267850 A and JP 06-292514 A, and KINEKAWA, Y. and KITABATAKE, N. "Biosci. Biotech. Biochem." Vol.51, 834 (1995), KITABATAKE, N., FUJITA, Y. and KINEKAWA, Y. "J. Food Sci." Vol.61, 500 (1996) and the like. The commercial products include "Genesis (trade name)" manufactured by Daiichi-Kasei Co., Ltd.

Such Process Whey Protein has many functional characteristics which cannot be obtained by other protein materials. For example, it gives a transparent viscous oily liquid showing newtonian behavior, a transparent sol and a transparent gel. Particularly, a transparent gel prepared by adding a salt and heating is not molten even when heated to as high a temperature as in a retort. A high temperature is not especially required for the preparation of sol or gel and it is enough to be 0° C. or higher. A gel can be formed even at room temperature.

Furthermore, Process Whey Protein does not gel by heating when no salt nor mineral is added to form a transparent viscous liquid.

Also, Process Whey Protein is a protein material excellent in emulsification stability and digestive property and high in effective nutritive value.

As the "scleroprotein" constituting the main components of the capsule membrane of the present invention, useful are collagen, collagen hydrolyzate and the like. As the "derived protein", useful are gelatin, low molecular weight gelatin, gelatin hydrolyzate and the like. As the "mucopolysaccharide", useful are chondroitin sulfate and hyaluronic acid. They can be used each alone or in combination. Particularly, gelatin is preferred for taste.

The "plasticizer" is not particularly restricted but the useful compounds are glycerol, polyglycerol, polyethylene glycol, propylene glycol and the like. They can be used each alone or in combination.

The amount of "Process Whey Protein" used is not especially restricted but is preferably 0.07 to 2 weight %, more preferably 0.1 to 1 weight %, based on the solid amount of the capsule membrane. Usually, a solution containing 7 to 10 weight % of Process Whey Protein is added in an amount of 1 to 20 weight %, preferably 1 to 10 weight %, based on the total amount of the raw materials for capsule membrane before drying for use.

The amount of scleroproteins, derived proteins and mucopolysaccharides used is also not particularly restricted but usually 40 weight % or more, particularly 60 to 99 weight % in the capsule membrane is preferred. It is preferably 5 to 50 weight % based on the total amount of the raw materials before drying.

The amount of the plasticizer used in the present invention may be 0 to 40 weight %, particularly 5 to 35 weight %, of the capsule membrane and usually it is preferred to use 10 to 30 weight % based on the total amount of the raw materials before drying.

The capsule of the present invention can be prepared by mixing a solution of Process Whey Protein with other materials and heating and drying it. The mixing can be carried out by dissolving or dispersing uniformly for example with stirring according to usual method. A jacketed stirring defoaming vessel can be used for simultaneously carrying out deaeration, stirring and heating.

The heating temperature for the mixture is preferably 50° C. or higher, particularly 70° to 100° C.

The succeeding drying process requires no special means and can be carried out by a usual method, for example by using an air flow type rotary dryer.

The moisture content of the membrane after is preferably 1 to 15 weight %, more preferably 3 to 10 weight %, most preferably 4 to 8 weight %.

The Process Whey Protein used in the present invention is prepared by heat-denaturing whey protein, which is a globular protein, under a specific condition to modify it to "a soluble linear aggregate".

When no salt is added, the Process Whey Protein aggregates repel each other by static repulsion and therefore it does not gel nor thickens when heated. However, when a salt is added, static repulsion between aggregates is weakened and the aggregates approach each other by intermolecular attraction and hydrophobic interaction and then a fine heat-irreversible gel network is formed by disulfide bond and S—S exchange. In the present invention, we have found that a gel network and a membrane can be easily formed by heat-drying Process Whey Protein even when no salt is added. As the result of utilizing the property of Process Whey Protein to improve the property of capsule product, we have found that a capsule prepared by adding at least one of scleroproteins, derived proteins and mucopolysaccharides to Process Whey Protein and further adding at least one plasticizer such as glycerol and then heating and drying has a far more excellent property than conventional ones.

Process Whey Protein forms a rigid gel and a membrane network by decreasing moisture content even when no salt is added and this fine heat-irreversible gel network can be formed even in a system where other proteins and polysaccharides are present to enhance total strength and heat-resistance of the gel. Thus, when used in the capsule membrane of the present invention, Process Whey Protein rapidly forms a membrane structure when the raw material is heated and then dried and the strength of the membrane is increased with no loss of transparency and the adhesion at the time of capsule formation is improved and also the formation of avec sphere and deformation can be prevented. This characteristic acts highly advantageously in the capsule forming process to make possible adhesion at a low temperature and to make thin the membrane thickness. It also acts positive on several properties of the prepared capsule including collapsing property in water, strength against compression and drying, and melting property by heating.

The molded capsule according to the present invention may be prepared in a die rolls encapsulating machine as shown, in the Examples, in which a viscous mixture containing Process Whey Protein with at least one selected from the group consisting of scleroproteins, derived proteins and mucopolysaccharides is prepared, a sheet for the capsule membrane is formed with the mixture, filling a fill material into the capsule membrane with rotary die rolls, capsules are punched out, and the capsules are cooled and dried. In the method, the sheet can be stably formed to have a wet thickness of 0.05 mm or more.

The molded capsule prepared according to the present invention can reduce the drying period and can improve the condition and the period for maintaining the quality of the product capsule and is beneficial to the view point of energy saving and effective use of resources.

PREFERRED EMBODIMENTS OF THE INVENTION

The following examples serve to illustrate the invention in more detail although the invention is not limited to the examples.

The chemicals, capsule-forming methods and test methods used in the examples are as follows.

[Capsule material]

A Process Whey Protein solution ("Genesis" manufactured by Daiichi Kasei Co., Ltd., Process Whey Protein content: 9% ), glycerol (manufactured by Nippon Yushi Co., Ltd.) and hot water are mixed together in a stirring defoaming vessel in which hot water is passed through the jacket, and gelatin (manufactured by Nitta Gelatin Co., Ltd.) is added and dissolved into the mixture, and then the mixture is defoamed in vacuo, and the viscosity was adjusted (by adding hot water when the viscosity is high, and by repeating the defoaming operation when it is low) and then the resultant solution is stored in a subdividing tank for about 6 hours (at 55 to 60° C.) for aging.

[Packing liquid]

Soybean oil—Purified soybean oil (manufactured by Linol Yushi Co., Ltd.) is filtered (50 mesh), or Chitosan suspension—1620 g of safflower oil (manufactured by Linol Yushi Co., Ltd.), 90 g of beeswax (manufactured by Serarika NODA Co., Ltd.) and 90 g of Poem S-100 (manufactured by Riken Vitamin Co., Ltd.) are dissolved at 70° C. by heating and then the liquid temperature is lowered to about 45° C., and 1000 g of chitosan (manufactured by Kimitsu Kagaku Kogyo Co., Ltd.) and 200 g of soybean lecithin (True Lecithin Kogyo Co., Ltd.) are added and the mixture is mixed by using a T.K.HOMO-MIXER (manufactured by Tokushu Kika Kogyo Co., Ltd.) (10000 rpm, 20 minutes, 40° C.) and then the solution is made into corpuscles or fine particles by using a T.K.MY-COLLOIDAR (manufactured by Tokushu Kika Kogyo Co., Ltd.) and filtered (50 mesh) and defoamed in vacuo.

[Capsule-forming method]

It was formed by a usual method with use of a rotary capsule-forming machine or a die rolls encapsulating machine (manufactured by Kamata Co., Ltd.). The used mold was OVAL type or OBLONG type. The sheet thickness described in the Examples is a wet thickness before punching out.

[Test of physical properties of the resultant preparation]

Appearance inspection—By visual observation.

Moldability—Assessed by an experienced operator.

Viscosity of capsule material—By a B type viscometer (manufactured by Tokyo Keiki Co., Ltd.), Collapsing test—Tested in accordance with J.P. collapsing test method.

Membranemoisture—Tested in accordance with J.P. drying loss test method by using an infrared moisture meter (manufactured by Kett Co., Ltd., FD-230 type).

Rupture load (strength against compression)—Tested by using a Kiya type hardness tester (manufactured by Fujiwara Seisakusho Co., Ltd., maximum load: 30 kg).

Stability test (accelerated)—Carried out by using a constant temperature constant moisture vessel (manufactured by Advantec Co., Ltd., AGX-226) and the extent of caking was observed.

EXAMPLE 1

By using the above-mentioned capsule material containing a Process Whey Protein solution and using a soybean oil or a chitosan suspension as the packing liquid, various type capsules A to K including OVAL type and OBLONG type as shown in Table 1 were prepared. As the result, in all conditions, those using Process Whey Protein, gelatin and glycerol as the capsule material gave good capsule formation. From these test results, it was apparent that the capsule using Process Whey Protein had an appearance and moldability equivalent to the conventional product.

TABLE 1

Transparency and Moldability of capsules prepared by using Process Whey Protein, gelatin and glycerol

|  | A | B | C | D | E | F | G | H | I | J | K |
|---|---|---|---|---|---|---|---|---|---|---|---|
| Capsule material |  |  |  |  |  |  |  |  |  |  |  |
| Gelatin (wt. parts) | 100 | 100 | 100 | 100 | 100 | 100 | 100 | 100 | 100 | 100 | 100 |
| Glycerol (wt. parts) | 20 | 30 | 35 | 50 | 50 | 50 | 50 | 50 | 50 | 50 | 50 |
| PWP (wt. parts) | 20 | 10 | 5 | 10 | 5 | 5 | 10 | 5 | 10 | 5 | 5 |
| Viscosity (× 1000 cps) | 15 | 15 | 15 | 20 | 15 | 15 | 20 | 15 | 20 | 15 | 15 |
| Sheet thickness (min) | 0.85 | 0.85 | 0.85 | 0.50 | 0.50 | 0.50 | 0.50 | 0.30 | 0.85 | 0.50 | 0.50 |
| Capsule form (No. 5) | OVAL | OVAL | OVAL | OVAL | OVAL | OBLONG | OBLONG | OBLONG | OBLONG | OBLONG | OBLONG |
| Packing liquid | S. O. | S. O. | S. O. | S. O. | S. O. | S. O. | S. O. | S. O. | C. | C. | C. |
| Packed amount (mg) | 250 | 250 | 250 | 250 | 250 | 250 | 250 | 250 | 250 | 250 | 250 |
| Transparency | Δ | ○ | ○ | ○ | ○ | ○ | ○ | ○ | ○ | ○ | ○ |
| Moldability | good | good | good | good | good | good | good | good | good | good | normal |

PWP: 9% solution of Process Whey Protein
Packing liquid:
S. O. Soybean oil
C. Chitosan suspension
Transparency:
○ transparent
Δ slightly turbid

COMPARATIVE EXAMPLE 1

Capsules C' to I' were prepared in the same manner as for capsules C to I in Example 1 except that a capsule material containing no Process Whey Protein solution was used.

Comparison Tests 1 to 6

Physical properties of the products prepared in Example 1 were compared to those prepared in Comparative Example 1 or conventional products.

[Comparison test 1]

The lowest temperature of the segment (heat supply equipment for the sheet) which can provide good adhesion was measured and the result is shown in Table 2.

TABLE 2

Adhesive property of sheet

| Sample | E | E' | F | F' |
|---|---|---|---|---|
| Mold (No. 5) | OVAL | OVAL | OBLONG | OBLONG |
| Glycerol (wt. parts) | 50 | 50 | 50 | 50 |
| Sheet thickness (mm) | 0.50 | 0.50 | 0.50 | 0.50 |
| PWP (wt. parts) [1) | 5 | 0 | 5 | 0 |
| Segment temperature (° C.) [2) | >31 | >34 | >32 | >36 |

[1) PWP: 9% aqueous solution of Process Whey Protein
[2) Various forming conditions were made to be same and the segment temperature giving enough adhesion strength was measured.

The products (E, F) of Examples in accordance with the present invention gave segment temperatures lower than those of the products (E', F') of Comparative Example by 3 to 4° C.

From the result, it was found that a capsule material prepared from Process Whey Protein, gelatin and glycerol can be adhered at a lower temperature than the conventional one and can avoid generation of avec sphere and deformation to improve adhesion property largely.

[Comparison test 2]

The capsule material was overdried and the rupture load at compression was measured. The result is shown in Table 3.

TABLE 3

Capsule strength when overdried

| Sample | D | D' | G | G' |
|---|---|---|---|---|
| Mold (No. 5) | OVAL | OVAL | OBLONG | OBLONG |
| Glycerol (wt. parts) | 50 | 50 | 50 | 50 |
| Sheet thickness (mm) | 0.50 | 0.50 | 0.50 | 0.50 |
| PWP (wt. parts) | 10 | 0 | 10 | 0 |
| Membrane moisture (%) | 4.5 | 4.3 | 4.0 | 4.3 |
| Rupture load (kg) | 25 | 14 | 27 | 15 |

PWP: 9% aqueous solution of Process Whey Protein

The products (D, G) of Example in accordance with the present invention were found to provide significantly higher strength than the products (D', G') of Comparative Example and hardly broken.

From the result, it was found that a capsule material using Process Whey Protein can prepare a thinner capsule than the conventional product.

[Comparison test 3]

A capsule was prepared by increasing the plasticizer to give softness and it was stood at 50° C. and at 40° C. and at a relative humidity of 75% and its property was examined. The results are shown in Tables 4 and 5.

From these results, it was found that the products (D, G) of Example according to the present invention hardly cake and are high in stability against heat and humidity compared to the products (D', G') of Comparative Example.

TABLE 4

Heat stability when the plasticizer is increased (50° C., closed vessel).

| Sample | D | D' | G | G' |
|---|---|---|---|---|
| Hold (No. 5) | OVAL | OVAL | OBLONG | OBLONG |
| Glycerol (wt. parts) | 50 | 50 | 50 | 50 |
| Sheet thickness (mm) | 0.50 | 0.50 | 0.50 | 0.50 |
| PWP (wt. parts) | 10 | 0 | 10 | 0 |
| Membrane moisture (%) | 5.3 | 5.3 | 5.4 | 5.3 |
| Caking | | | | |
| 1 hour | − | − | − | − |
| 2 | − | − | − | + |
| 3 | − | + | − | + |
| 4 | − | + | − | + |
| 5 | − | + | − | + |
| 6 | − | + | − | ++ |
| 7 | − | + | − | ++ |
| 8 | − | + | − | ++ |

PWP: 9% aqueous solution of Process Whey Protein
Criteria
−: No caking. (Detached by low impact)
+: Slight caking. (Somewhat difficult to be broken by low impact)
++: Intermediate caking. (Remarkable mass though somewhat broken by low impact)

TABLE 5

Temperature stability of capsule when the plasticizer is increased (temperature: 40° C., humidity: 75%, open vessel).

| Sample | D | D' | G | G' |
|---|---|---|---|---|
| Mold (No. 5) | OVAL | OVAL | OBLONG | OBLONG |
| Glycerol (wt. parts) | 50 | 50 | 50 | 50 |
| Sheet thickness (mm) | 0.50 | 0.50 | 0.50 | 0.50 |
| PWP (wt. parts) | 10 | 0 | 10 | 0 |
| Membrane moisture (%) | 5.3 | 5.3 | 5.4 | 5.3 |
| Caking | | | | |
| 1 hour | − | − | − | − |
| 2 | − | − | − | − |
| 3 | − | + | − | + |
| 4 | + | ++ | + | + |
| 5 | ++ | +++ | + | ++ |
| 6 | +++ | +++ | ++ | +++ |
| 7 | +++ | +++ | +++ | +++ |

PWP: 9% aqueous solution of Process Whey Protein
Criteria
−: No caking. (Detached by low impact)
+: Slight caking. (Somewhat difficult to be broken by low impact)
++: Intermediate caking. (Remarkable mass though somewhat broken by low impact)
+++: Heavy caking (Capsule is not broken by impact)

[Comparison test 4]

The collapsing property of the capsule with water was investigated. The result is shown in Table 6. It was found that the products (C, I) of Example according to the present invention require longer period until collapsing (opening) than the products (C', I') of Comparative Example, but collapsed in shorter period than those of Comparative Example.

From the result, it was found that the capsule material prepared from Process Whey Protein, gelatin and glycerol could give a capsule which has an excellent property in that it was difficult to be broken in the mouth and collapsed more rapidly in digestive organs.

TABLE 6

Collapsing property of capsule against water (37° C.)

| Sample | C | C' | I | I' |
|---|---|---|---|---|
| Mold (No. 5) | OVAL | OVAL | OBLONG | OBLONG |
| Glycerol (wt. parts) | 35 | 35 | 50 | 50 |
| Sheet thickness (mm) | 0.85 | 0.85 | 0.85 | 0.850 |
| Packing liquid | Soybean oil | | Chitosan | |
| PWP (wt. parts) [1] | 5 | 0 | 10 | 0 |
| Opening (minutes) [2] | 2~3 | 1~2 | 1~2 | 2~3 |
| Collapsing (minutes) [3] | 6~7 | 7~11 | 6~8 | 8~11 |

[1] PWP: 9% aqueous solution of Process Whey Protein
[2] Period until the capsule is open
[3] Period until the capsule collapses (is dissolved)

[Comparison test 5]

The relationship between sheet thickness (membrane thickness) of the capsule and drying period was tested. The result is shown in Table 7. The products (G, H) of Example according to the present invention could be prepared stably to a sheet thickness of 0.3 to 0.5 mm but the capsule material of the conventional product was difficult to prepare such a thin membrane. Also, the period required for drying the capsule material of the products (G, H) according to the present invention came to be far shorter as the sheet could be made thinner than the conventional product.

From these results, it was found that the capsule material prepared from Process Whey Protein, gelatin and glycerol could be made thinner than the conventional product and therefore the capsule form could be made smaller and thus it could be dosed easily and it could collapse more rapidly in digestive tracts and hence the packed material could be exposed in the digestive tracts in a shorter time, that is, it gave an immediate effect. Also, as the sheet can be made thinner in the preparation of capsule, the drying period can be reduced to improve productivity.

TABLE 7

Sheet thickness of capsule and drying period

| Sample | G | H | Conventional product [2] |
|---|---|---|---|
| Mold (No. 5) | OBLONG | OBLONG | OBLONG |
| Glycerol (wt. parts) | 50 | 50 | 35 |
| Sheet thickness (mm) | 0.50 | 0.30 | 0.85 |
| PWP (wt. parts) [1] | 10 | 5 | 0 |
| Membrane moisture (%) | | | |
| Drying period | | | |
| 1 hour | 13.1 | 9.0 | 17.7 |
| 3 hours | 9.8 | 7.0 | 11.6 |
| 5 hours | 8.5 | 6.2 | 10.5 |
| 24 hours | 6.0 | 4.7 | 8.7 |
| 48 hours | 5.4 | 4.3 | 7.3 |

[1] PWP: 9% aqueous solution of Process Whey Protein
[2] Prepared from gelatin and glycerol

EXAMPLE 2

A bath capsule was prepared in the same manner as in Example 1 and the properties were evaluated in the same manner as in Example 1. The mold used was No. 90 ROUND for bath capsule.

The test result for physical properties of a bath capsule (L) prepared by using Process Whey Protein, gelatin and glycerol according to the present invention is shown in Table 8 compared with a conventional product.

While preparation of a practically usable capsule was difficult at a sheet thickness of 0.65 mm by using the conventional material, the product (L) using the Process Whey Protein could be made to a sheet thickness of 0.65 mm. Also, it was found that the product (L) of the present invention is difficult to cake compared to the conventional product and also is good in collapsing property. This feature is useful as a bath capsule.

TABLE 8

Characteristics of bath capsule prepared by using Process Whey Protein

|  | L | Conventional product *2) |
|---|---|---|
| Capsule material |  |  |
| Gelatin (wt. parts) | 100 | 100 |
| Glycerol (wt. parts) | 50 | 50 |
| PWP (wt. parts) *1) | 10 | — |
| Sheet thickness (mm) | 0.65 | 0.90 |
| Capsule form (No. 90 mold) | ROUND | ROUND |
| Packing liquid | Soybean oil |  |
| Packed amount (mg) | 6000 | 6000 |
| Capsule material moisture (%, 24 hours) | 6.8 | 7.2 |
| Transparency | Transparent |  |
| Collapsing period (40° C., min.) | <1 | <2 |

*1) PWP: 9% solution of Process Whey Protein
*2) Prepared from gelatin and glycerol

EXAMPLE 3

By using low molecular weight gelatin (manufactured by Nitta Gelatin Co., Ltd., 114 Brume) said generally to be unsuitable for the preparation of capsule, capsules (M, N, O) were prepared in the same manner as in Example I and, at the same time, capsules (M', N', O') of Comparative Example using no Process Whey Protein in the capsule material were prepared.

The property of these capsules is shown in Table 9. From the result, it was found that, while the products (M, N, O) according to the present invention gave capsules which had a sheet thickness of 0.50 to 0.85 mm and was transparent and excellent in collapsing property by water and showed high strength, the products (M', N', O') of Comparative Example prepared by not using Process Whey Protein were unmoldable and showed a property difficult in practical production.

From this result, a relatively high molecular weight gelatin has been usually used for the preparation of capsules. However, the high molecular weight gelatin has drawbacks in solubility and loses viscosity remarkably by hydrolysis immediately after the preparation and therefore an aging process is essential for a long period and also the viscosity decreases during use thereafter and fine adjustment of forming condition is unavoidable. On the other hand, low molecular gelatin is excellent in solubility but is low in apparent viscosity and is very low in forming aptitude of the capsule. A capsule material prepared by using Process Whey Protein and low molecular gelatin is high in solubility and experiences minute reduction in viscosity as the time passes and is high in forming aptitude. From these facts, it was found that the aging process could be largely reduced to improve productivity.

TABLE 9

Properties of capsules prepared by using low molecular gelatin

|  | M | M' | N | N' | O | O' |
|---|---|---|---|---|---|---|
| Capsule material |  |  |  |  |  |  |
| LM gelatin (wt. parts)*1) | 100 | 100 | 100 | 100 | 100 | 100 |
| Glycerol (wt. parts) | 50 | 50 | 50 | 50 | 50 | 50 |
| PWP (wt. parts)*2) | 10 | 0 | 10 | 0 | 10 | 0 |
| Viscosity (× 1000 cps) | 20 | 10 | 10 | 10 | 10 | 10 |
| Sheet thickness (mm) | 0.30 | 0.30 | 0.50 | 0.50 | 0.50 | 0.50 |
| Capsule form (No. 5 mold) | OBLONG | OBLONG | OBLONG | OBLONG | OBLONG | OBLONG |
| Packing liquid | Soybean oil |  |  | Chitosan |  |  |
| Packed amount (mg) | 250 | 250 | 250 | 250 | 250 | 250 |
| Capsule material moisture (%, 48 hours) | 4.3 |  | 4.7 | 4.5 | 4.7 |  |
| Membrane breaking load (kg) | 15 |  | 23 |  | 14 | 22 |
| Transparency | Transparent |  |  | Transparent |  |  |
| Collapsing period (min) | 1~2 |  | 1~4 | 2~4 | 2~5 |  |
| Moldability*3) | Δ | x | ⊙ | Δ | ⊙ | x |

*1)LM gelatin: Low molecular gelatin
*2)PWP: 9% solution of Process Whey Protein
*3)⊙: Good moldability, Δ: Defect in productivity, x: Not moldable

EXAMPLE 4

Capsules were prepared in the same manner as in Example 1 by using no plasticizer and using a capsule material consisting of Process Whey Protein, gelatin and water.

While a capsule using no plasticizer could not be prepared by the prior art, the method of the present invention gave capsules (P, Q) excellent in transparency and high in forming aptitude as shown in Table 10 even with no addition of a plasticizer.

TABLE 10

Properties of capsules prepared by using no plasticizer

|  | P | Q |
|---|---|---|
| Capsule material |  |  |
| Gelatin (wt. parts) | 100 | 100 |
| PWP (wt. parts) | 15 | 20 |
| Viscosity (× 1000 cps) | 18 | 18 |
| Sheet thickness (mm) | 0.85 | 0.85 |
| Capsule form (No. 5) | OVAL | |
| Packing liquid | Soybean oil | |
| Packed amount (mg) | 250 | |
| Transparency | Transparent | |
| Moldability | Normal | |

PWP: 9% solution of Process Whey Protein

EXAMPLE 5

Capsules were prepared in the same manner as in Example 1 by using polyethylene glycol (manufactured by Nippon Yushi Co., Ltd., #400) or polyglycerol (manufactured by Sakamoto Yakuhin Kogyo Co., Ltd., #500) as the plasticizer.

As shown in Table 11, the present invention could prepare products excellent in transparency and forming property even in the case where polyethylene glycol or polyglycerol was used as the plasticizer.

TABLE 11

Properties of capsules prepared by using polyethylene glycol and polyglycerol

|  | R | S | V | W |
|---|---|---|---|---|
| Capsule material |  |  |  |  |
| Gelatin (wt. parts) | 100 | 100 | 100 | 100 |
| PEG (#400) (wt. parts) [1] | 20 | 30 | 50 | 0 |
| Polyglycerol (#500) (wt. parts) | 0 | 0 | 0 | 30 |
| PWP (wt. parts) [2] | 20 | 10 | 5 | 10 |
| Viscosity (× 1000 cps) | 15 | 15 | 15 | 20 |
| Sheet thickness (mm) | 0.85 | 0.85 | 0.85 | 0.85 |
| Capsule form (No. 5 mold) | OVAL | | | |
| Packing liquid | Soybean oil | | | |
| Packed amount (mg) | 250 | | | |
| Transparency | Somewhat turbid | | Transparent | |
| Moldability | Good | | Normal | |

[1] PEG (#400): polyethylene glycol having an average molecular weight of 400.
[2] PWP: 9% solution of Process Whey Protein.

According to the present invention, it became possible to prepare a capsule membrane for foods, drugs and cosmetics which has a highly improved adhesion of membrane sheet used in the preparation of capsules and is formable at a lower temperature and can avoid generation of G tin sphere and deformation and scarcely broken under an overdried condition as the membrane strength is increased and is stable against heat and moisture and difficult to cake and excellent in collapsing property in digestive tracts.

Also, in the present invention, it became possible to prepare a capsule which has thin membrane and is smaller and easy to be taken and rapidly digested and softer and difficult to cake and also a product containing no plasticizer.

Furthermore, according to the present invention, it became possible to use protein material which has been difficult to be used conventionally as the capsule material and to save the resources, time and energy as the capsule for the preparation of capsules.

What is claimed is:

1. A capsule having a capsule membrane which contains a mixture of Process Whey Protein together with at least one selected from the group consisting of scleroproteins, gelatin, low molecular weight gelatin, gelatin hydrolytic and mucopolysaccharides, said capsule being a molded capsule, said capsule having seams, and said capsule membrane formed from a sheet having a wet thickness of 0.05 mm or more.

2. The capsule of claim 1 wherein the capsule membrane contains a plasticizer.

3. The capsule of claim 1 wherein the capsule membrane contains Process Whey Protein in an amount of 0.07 to 2 weight % on a dry basis.

4. The capsule of claim 1 wherein the capsule membrane contains scleroproteins, gelatin, low molecular weight gelatin, gelatin hydrolyzate and/or mucopolysaccharides in an amount of 40 weight % or more on a dry basis.

5. The capsule of claim 2 wherein the plasticizer is at least one selected from the group consisting of glycerol, polyglycerol, polyethylene glycol and propylene glycol.

6. The capsule of claim 1 having a capsule membrane moisture content of 3 to 10 weight %.

7. The capsule of claim 1 wherein the capsule membrane contains scleroproteins, gelatin low molecular weight gelatin, gelatin hydrolyzate and/or mucopolysaccharides in an amount of 60 to 99 weight % on a dry basis.

8. The capsule of claim 1 having a capsule membrane moisture content of 1 to 15 weight %.

* * * * *

UNITED STATES PATENT AND TRADEMARK OFFICE
CERTIFICATE OF CORRECTION

PATENT NO. : 6,333,047 B1
DATED : December 25, 2001
INVENTOR(S) : Katagihara et al.

It is certified that error appears in the above-identified patent and that said Letters Patent is hereby corrected as shown below:

Column 2,
Line 6, please change "are" to -- is --
Line 12, please delete both occurrences of "a"

Column 3,
Line 18, please change "after is" to -- after drying is --

Column 4,
Line 62, please change "Membranemoisture" to -- Membrane moisture --

Column 12,
Line 3, please change "G tin" to -- avec --
Line 29, please change "hydrolytic" to -- hydrolyzate --
Line 52, please change "gelatin low" to -- gelatin, low --

Signed and Sealed this

Thirteenth Day of August, 2002

*Attest:*

JAMES E. ROGAN
*Attesting Officer*   *Director of the United States Patent and Trademark Office*